US006201145B1

(12) United States Patent
Fan

(10) Patent No.: US 6,201,145 B1
(45) Date of Patent: *Mar. 13, 2001

(54) NON-HYDROGENATED CANOLA OIL FOR FOOD APPLICATIONS

(75) Inventor: Zhegong Fan, Delran, NJ (US)

(73) Assignee: Cargill, Incorporated, Wayzata, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/304,366

(22) Filed: May 4, 1999

Related U.S. Application Data

(63) Continuation of application No. 08/425,108, filed on Apr. 20, 1995, now Pat. No. 5,969,169, which is a continuation-in-part of application No. PCT/US94/04352, filed on Apr. 26, 1994, which is a continuation-in-part of application No. 08/184,128, filed on Jan. 21, 1994, now abandoned, which is a continuation-in-part of application No. 08/054,806, filed on Apr. 27, 1993, now abandoned.

(51) Int. Cl.$^7$ ............................. C07C 53/00; C07C 57/00
(52) U.S. Cl. ................................ 554/224; 554/8; 554/9; 554/12; 554/223
(58) Field of Search ............................. 554/8, 9, 12, 223, 554/224

(56) References Cited

U.S. PATENT DOCUMENTS

| 4,627,192 | 12/1986 | Fick | 47/58 |
| 5,969,169 | * 10/1999 | Fan | 554/223 |

FOREIGN PATENT DOCUMENTS

| 323 753 | 7/1989 | (EP) . |
| WO 90/10380 | 9/1990 | (WO) . |
| WO 91/15578 | 10/1991 | (WO) . |
| WO 92/03919 | 3/1992 | (WO) . |
| WO 93/06714 | 4/1993 | (WO) . |
| WO 93/17566 | 9/1993 | (WO) . |

OTHER PUBLICATIONS

Warner et al., *JAOCS*, 66(4):558–564, 1989.
Eskin et al., *JAOCS*, 66(8):1081–1084, 1989.
Scarth et al., *Can. J. Plant Sci.*, 68:509–511, 1988.
Prevot et al., *JAOCS*, 67(3):161–164, 1990.
Neff et al., Paper: "Oxidative Stabilities of Oils from Selected Canola Varieties", 84th American Oil Chemists' Society Annual Meeting, Anaheim, Calif., Apr. 24–29, 1993 (Abstract).
Nitsch, *Angew. Bokanik*, 50:31–42, 1976.
Rakow, *Z. Pflanzenzuchtg*, 69:62–82, 1973.
Mounts et al., "Handbook of Soy Oil Processing and Utilization", Ch. 15, 245–266, 1980.
Mounts, *JAOCS*, 56:659–663, 1979.
Bailey's Industrial Oil and Fat Products, 2:452 (4th Ed.), 1982.
A.O.C.S Official method Cd 12–57, pp. 1–4, 1989.
A.O.C.S. Recommended Practice Cg 2–83, pp. 1–3, 1989.
Laubli et al., *JAOCS*, 63(6):792–795, 1986.
deMan et al., *JAOCS*, 64(7):993–996, 1987.
Morrison et al., *JAOCS*, 55:451–453, 1978.
White et al., *JAOCS*, 65(8):1334–1338, 1988.
Purdy, *JAOCS*, 61:523–525, 1985.
Mounts et al., *JAOCS*, 65(4):624–628, 1988.
Karleskind et al., *Lavoisier Tec & Doc*, pp. 1212–1215, 1992.
Kirk–Othmer, Encyclopedia of Chemical Technology, pp. 795–831, 1978.
Boyeldieu, *Lavoisier–tec & Doc*, Chapter II, pp. 17–65, 1991.

* cited by examiner

*Primary Examiner*—Deborah Carr
(74) *Attorney, Agent, or Firm*—Fish & Richardson, P.C.

(57) ABSTRACT

A non-hydrogenated canola oil having superior oxidative stability and fry stability useful for food applications is disclosed, as well as seeds, plant lines and progeny thereof from which the oil is derived.

8 Claims, No Drawings

NON-HYDROGENATED CANOLA OIL FOR FOOD APPLICATIONS

CROSS-REFERENCE TO RELATED APPLICATION

This application is a continuation of U.S. application Ser. No. 08/425,108, filed Apr. 20, 1995 now U.S. Pat. No. 5,969,169, which is a continuation-in-part application of PCT/US94/04352, filed Apr. 26, 1994 claiming priority under 35 USC §120, which is a continuation-in-part application of Ser. No. 08/184,128 filed Jan. 21, 1994, now abandoned, which is a continuation-in-part of Ser. No. 08/054,806 filed Apr. 27, 1993, now abandoned.

FIELD OF THE INVENTION

The present invention relates to non-hydrogenated canola oil having improved flavor and performance attributes especially suitable for food applications, and to the Brassica seeds, plant lines and progeny thereof from which the oil is derived.

BACKGROUND

Canola oil has the lowest level of saturated fatty acids of all vegetable oils. As consumers become more aware of the health impact of lipid nutrition, consumption of canola oil in the U.S. has increased. However, generic canola oil has limited use in deep frying operations, an important segment of the food processing industry, due to its instability. Canola oil extracted from natural and commercial varieties of rapeseed contains a relatively high (8%–10%) α-linolenic acid content ($C_{18:3}$) (ALA). The oil is unstable and easily oxidized during cooking, which in turn creates off-flavors of the oil and compromises the sensory characteristics of foods cooked in such oils. It also develops unacceptable off odors and rancid flavors during storage.

Hydrogenation can be used to improve performance attributes by lowering the amount of linoleic and α-linolenic acids in the oil. In this process the oil increases in saturated and trans fatty acids, both undesirable when considering health implications. Blending of oil can also be used to reduce the α-linolenic acid content and improve the performance attributes. Blending canola oil with other vegetable oils such as cottonseed will increase the saturated fatty acids content of the oil but decreases the healthy attributes of canola oil.

α-Linolenic acid has been reported to oxidize faster than other fatty acids. Linoleic and α-linolenic acids have been suggested as precursors to undesirable odor and flavor development in foods. To improve the functionality of canola oil, the University of Manitoba developed the canola variety "Stellar" which has reduced α-linolenic acid (Scarth et al., Can. J. Plant Sci., 68:509–511 (1988)). The low α-linolenic acid oil was reduced in odor when heated in air, but still remained unacceptable to the sensory panel in flavor evaluations (Eskin et al., J. Am. Oil Chem. Soc. 66:1081–1084 (1989)). The oxidative stability of Stellar oil increased by 17.5% over the commercial variety Westar as measured by Active Oxygen Method (AOM) hours. (Can. J. Plant Sci. (1988) Vol. 68, pp. 509–511).

European Patent Application, EP 0 323 753 A1 describes a canola oil having an enhanced oleic acid content with increased heat stability in combination with other traits. The application further describes a frying oil with reduced α-linolenic acid which imparts increased oxidative stability. No flavor and performance testing with the described oil was reported.

Data which shows that oxidative stability is not solely related to fatty acid composition (described below) indicates that increased stability cannot be inferred from fatty acid composition. The amount of α-linolenic acid in the oil is only one factor which controls oxidative stability and flavor stability. Thus a canola oil which has improved stability in its flavor and performance attributes for use in food operations is needed. The present invention provides such an oil.

SUMMARY OF THE INVENTION

The present invention provides an oil comprising a non-hydrogenated canola oil having an oxidative stability of from about 37 to about 40 AOM hours in the absence of antioxidants. The oil of the present invention also has fry stability for up to at least 64 hours. After 64 hours of frying, the oil of the present invention has reduced total polar material content of about 23%, reduced free fatty acid content of about 0.7%, reduced red color development as shown by a Lovibond color value of 6.7 red and reduced para-anisidine value of 125 absorbance/g. After 32 hours of frying, the oil of the present invention has reduced total polar material content of about 12%, reduced free fatty acid content of about 0.3%, reduced red color development as shown by a Lovibond color of 2.7 red and reduced para-anisidine value of 112 absorbance/g.

The present invention further provides a seed comprising a *Brassica napus* variety containing canola oil as described above, and progeny thereof.

The present invention further provides a plant line comprising a *Brassica napus* canola variety which produces canola oil as described above, and individual plants thereof.

BRIEF DESCRIPTION OF THE SEED DEPOSIT

Seed designated IMC 130 as described hereinafter was deposited on Apr. 16, 1993 with the American Type Culture Collection, MANASSAS Va. and was assigned accession number 75446.

DETAILED DESCRIPTION OF THE INVENTION

The present invention provides canola oil having superior stable flavor and performance attributes when compared to known canola oils. The invention also provides *Brassica napus* seeds, and plant lines producing seeds, from which such an oil can be produced.

A canola oil of the present invention is superior in oxidative stability and fry stability compared to known canola oils. The superior functionalities of the oil can be demonstrated, e.g., by standardized American Oil Chemists' Society (AOCS) oil testing methods. The improved characteristics of the oil permit it to be used in new food products and permit the oil to be used without hydrogenation in situations where increased flavor stability, oxidative stability, fry stability and shelf-life stability are desirable.

In the context of this disclosure, a number of terms are used. As used herein, "functionality" or "performance attributes" means properties or characteristics of the canola oil and includes flavor stability, fry stability, oxidative stability, shelf-life stability, and photooxidative stability.

Oxidative stability relates to how easily components of an oil oxidize which creates off-flavors in the oil, and is measured by instrumental analysis using accelerated oxidation methods. American Oil Chemists' Society Official Method Cd 12-57 for Fat Stability: Active Oxygen Method (re'vd 1989); Rancimat (Laubli, M. W. and Bruttel, P. A., JOACS 63:792–795 (1986)); Joyner, N. T. and J. E. McIntyre, Oil and Soap (1938) 15:184 (modification of the Schaal oven test). Oils with high oxidative stability are considered to be premium oils for shelf stable applications in foods, i.e., spray coating for breakfast cereals, cookies, crackers, fried foods such as french fries, and snack foods such as potato chips.

Fry stability relates to the resistance to degeneration of the oil during frying. Fry stability can be evaluated by measuring parameters such as total polar material content, free fatty acid content, color development and aldehyde generation. "Fry life" is determined by sequentially frying products in an oil and performing a sensory analysis of the flavor of the fried products. Fry life is measured as the length of time the oil is used for frying before the sensory analysis of a fried product degrades to a predetermined score. Oils for restaurants, hospitals and large institutions primarily are used for frying foods and require fry stability.

Flavor stability is determined by sensory analysis of an oil sample periodically taken from an oil held under defined conditions. For example, oils may be stored in an oven at an elevated temperature to accelerate the aging. The oil may also be stored at room temperature. However, the length of time required for testing renders this method to be less useful. Flavor stability is measured by the time it takes for the flavor of the oil to degrade to an established numerical score. The sensory panel rates the oil or food product from 1 (unacceptable) to 9 (bland). A rejection point is selected where the oil or food product begins to show deterioration. Bottled cooking oils and salad dressings require high flavor stability.

Photooxidative stability is determined from analysis of oil samples taken periodically from oil stored under defined light and temperature conditions. Photooxidative stability is reflected in the duration of time it takes for the flavor of the oil to degrade to a set score. Bottled cooking oils require high photooxidative stability.

Shelf-life stability is determined by the analysis of food samples cooked in the oil, then packaged and stored in an oven at an elevated temperature to accelerate aging. "Shelf-life" is the time it takes for the flavor of the food to degrade to give a set score. Oils for fried snacks require shelf-life stability.

As used herein, a "line" is a group of plants that display little or no genetic variation between individuals for at least one trait of interest. Such lines may be created by several generations of self-pollination and selection, or vegetative propagation from a single parent using tissue or cell culture techniques. As used herein, the terms "cultivar" and "variety" are synonymous and refer to a line which is used for commercial production.

"Saturated fatty acid" refers to the combined content of palmitic acid and stearic acid. "Polyunsaturated fatty acid" refers to the combined content of linoleic and α-linolenic acids. The term "room odor" refers to the characteristic odor of heated oil as determined using the room-odor evaluation method described in Mounts (J. Am. Oil Chem. Soc., 56:659–663, 1979).

A "population" is any group of individuals that share a common gene pool. The term "progeny" as used herein means the plants and seeds of all subsequent generations resulting from a particular designated generation.

The term "selfed" as used herein means self pollinated.

"Generic canola oil" refers to a composite blend of oils extracted from commercial varieties of rapeseed currently known, which varieties generally exhibited at a minimum 8–10% α-linolenic acid content, a maximum of 2% erucic acid and a maximum of 30 μmol/g total glucosinolate level. The seed from each growing region is graded and blended at the grain elevators to produce a uniform product. The blended seed is then crushed and refined, the resulting oil being a blend of varieties and sold for use. Table 1 shows the distribution of canola varieties seeded as percentage of all canola seeded in Western Canada in 1990. Canada is a leading producer and supplier of canola seed and oil.

TABLE 1

Distribution of Canola Varieties Grown in Western Canada in 1990

| Canola Variety | Percent of Seeded Area |
|---|---|
| B. campestris | |
| Candle | 0.4 |
| Colt | 4.4 |
| Horizon | 8.5 |
| Parkland | 2.5 |
| Tobin | 27.1 |
| B. napus | |
| Alto | 1.1 |
| Delta | 0.9 |
| Global | 0.9 |
| Legend | 18.2 |
| Pivot | 0.1 |
| Regent | 0.5 |
| Stellar | 0.2 |
| Tribute | 0.4 |
| Triton | 0.7 |
| Triumph | 0.2 |
| Westar | 29.5 |
| Others | 4.4 |

Source: Quality of Western Canadian Canola - 1990 Crop Year. Bull. 187, Declereg et al., Grain Research Laboratory, Canadian Grain Commission, 1404–303 Main Street, Winnipeg, Manitoba, R3C 3G8.

"Canola" refers to rapeseed (Brassica) which has an erucic acid ($C_{22:1}$) content of at most 2 percent by weight based on the total fatty acid content of a seed, preferably at most 0.5 percent by weight and most preferably essentially 0 percent by weight and which produces, after crushing, an air-dried meal containing less than 30 micromoles (μmol) per gram of defatted (oil-free) meal.

The term "canola oil" is used herein to describe an oil derived from the seed of the genus Brassica with less than 2% of all fatty acids as erucic acid.

Genetic crosses are made with defined germplasm to produce the canola oil of the present invention having reduced polyunsaturated fatty acids, improved flavor stability, fry stability, oxidative stability, photooxidative stability and shelf-life stability, in a high yielding Spring canola background. IMC 129, a Spring canola variety with high oleic acid in the seed oil is crossed with IMC 01, a Spring canola variety with low α-linolenic acid in the seed oil. Flower buds of the $F_1$ hybrid are collected for microspore culture to produce a dihaploid population. The dihaploid plants (genetically homozygous) are selected with high oleic, and reduced linoleic and α-linolenic acids in the seed oil and field tested for stability of the fatty acids and yield.

After five generations of testing in the field and greenhouse a high yielding selection with fatty acid stability in multiple environments is selected. Seed of selection is grown in isolation, harvested, and the oil extracted and processed to produce a refined, bleached and deodorized oil using known techniques. The oil produced was found to be functionally superior in oxidative stability and fry stability relative to a commercial-type, generic canola oil processed under similar conditions.

The canola oil of the present invention has an oxidative stability as determined by Active Oxygen Method (AOM) values of from about 35 to about 40 hours. This is significantly higher than any known pilot plant or commercial processed canola oil. The increase is 45 to 60% above commercial type generic canola oil.

Under extended frying conditions, canola oil of the invention is significantly lower than commercial-type generic canola in the oxidative tests for total polar material, free fatty acids, color development and p-anisidine value. The oil remains significantly lower in all oxidative parameters tested after 32 and 64 hours of frying.

The oil has about 12% and about 23% total polar materials at 32 and 64 hours of frying, respectively. This represents a 34% decrease at 32 hours and a 17% decrease at 64 hours compared to commercial type generic canola oil. The total polar materials are a measure of the total amount of secondary by-products generated from the triacylglycerols as a consequence of oxidations and hydrolysis, and their reduction indicates improved oxidative stability.

Oil of the invention has a reduced content of free fatty acids of about 0.3% and about 0.7% at 32 and 64 hours of frying, respectively. This represents a 37% decrease at 32 hours and a 23% decrease at 64 hours compared to commercial type generic canola oil. The level of free fatty acids is a measure of oxidation and hydrolysis of the triacylglycerols and their reduction also indicates improved oxidative stability.

The color developed in an oil during frying is also an indication of triacylglycerol oxidation. The oil of the present invention demonstrated a reduced level of color development. The Lovibond color is about 2.7 red and about 6.7 red at 32 and 64 hours of frying, respectively. This represents a 38% decrease at 32 hours and a 47% decrease at 64 hours compared to commercial type generic canola oil.

Reduced development of aldehydes during frying also indicate improved oxidative stability and are measured by the p-anisidine value in absorbance/g at 350 nm. The oil has a p-anisidine value of about 112 absorbance/g after 32 hours of frying and of about 125 absorbance/g after 64 hours of frying. This represents a 32% decrease at 32 hours and a 14% decrease at 64 hours compared to commercial type generic canola oil.

The oil additionally has improved oxidative stability and frying stability without hydrogenation or the addition of antioxidants. The improved oxidative and fry stability results in increased flavor stability of the oil. Addition of antioxidants to the oil will further increase oxidative stability.

Oil of the invention may be produced from, for example, a *Brassica* napus plant designated as IMC 130 or from a *Brassica mapus* line designated as A13.30137. The seed oil has reduced amounts of total $C_{16:0}$ (palmitic) and $C_{18:0}$ (stearic) saturates of less than 6.5%, oleic acid from 74 to 80%, linoleic acid from 5 to 12%, α-linolenic acid from 2.0 to 5.0% and erucic acid of less than 1%.

The oil of the present invention is especially suitable for use in food applications, in particular for frying foods, due to its superior oxidative stability and fry stability. Due to its non-hydrogenated nature, it is especially desirable for positive human health implications. The seeds, plant lines, and plants of the present invention are useful for the production of the non-hydrogenated canola of this invention.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only.

Example 1

A cross of IMC 129×IMC 01 was conducted to obtain A13.30038, a dihaploid Spring canola variety. IMC 129 (U.S. PVP Certificate No. 9100151) is a Spring canola *Brassica napus* variety possessing high oleic acid (>75%) in the seed oil. IMC 01 is a Spring canola *Brassica mapus* variety possessing low α-linolenic acid (<2.5%) in the seed oil. A genetic cross was made in 1989 to combine the low α-linolenic and high oleic acid traits in a high yielding background for commercial production.

The $F_1$ plants (IMC 129×IMC 01) were grown in a growth chamber at 12°/6° C. (day/night) with 16 hours of illumination. Flower buds between 2–3.5 mm were selected for microspore isolation. The microspores were isolated and cultured to produce embryos using the method of Lichter, R., Z. Pflanzenphysiol, 105:427–434 (1982). Plants regenerated from the microspores were grown in the greenhouse until flowering. Haploid plants were treated with colchicine to induce chromosome doubling. Dihaploid plants were self-pollinated.

Seed ($DH_1$) of the selfed dihaploid plants were harvested in 1990 and analyzed in bulk for fatty acid composition via gas chromatography. Following fatty acid analysis, seed designated A13.30038 was identified with high oleic and low α-linolenic acids (Table 2). The $DH_1$ seed was planted in the greenhouse and self-pollinated. The harvested $DH_2$ seed generation maintained the selected fatty acid composition. In 1991 the $DH_2$ seed was planted in Southeast Idaho to determine yield of the line. Plants in the field were self-pollinated to determine fatty acid stability. The $DH_3$ seed maintained the selected fatty acid composition in the field. $DH_3$ seed of A13.30038 was increased under isolation tents during the Winter of 1991 in Southern California. The $DH_4$ seed maintained the selected fatty acid stability and was increased in isolation (2 miles) in Southeastern Idaho during 1992 to further test oil quality and yield.

After the 1992 summer trial, A13.30038 was found to have improved yield and stable fatty acid composition. This line was renamed IMC 130. Yield data for line IMC130 is shown in Tables 13 and 14; the fatty acid composition over five generations is listed in Table 2.

TABLE 2

Fatty Acid Composition of
A13.30038 over Five Generations
Fatty Acid Composition

| Generation | $C_{16:0}$ | $C_{18:0}$ | $C_{18:1}$ | $C_{18:2}$ | $C_{18:3}$ | $C_{22:1}$ |
|---|---|---|---|---|---|---|
| $DH_1$ | 3.8 | 2.8 | 80.5 | 6.6 | 2.3 | 0.0 |
| $DH_2$ | 3.8 | 2.8 | 77.8 | 8.4 | 3.3 | 0.0 |
| $DH_3$ | 3.6 | 2.2 | 80.0 | 7.5 | 2.8 | 0.0 |
| $DH_4$ | 3.3 | 1.9 | 79.3 | 8.9 | 3.6 | 0.0 |
| $DH_5$ | 3.6 | 2.9 | 76.2 | 10.3 | 3.4 | 0.0 |

The IMC 130 seed was crushed and the resulting oil processed using a pilot plant at the POS Pilot Plant Corporation, 118 Veterinary Road, Saskatoon, Saskatchewan, Canada. The starting seed weight was 700 kg. All oils for which data is supplied were prepared under the same conditions set forth below. To ensure good extraction of the oil the seed was tempered by spraying the seed with water to raise the moisture to 8.5%. The seed and water were blended and allowed to equilibrate. The seed was flaked using smooth roller. A minimum gap setting was used to produce a flake thickness of 0.23 to 0.27 mm. The oil cells were further ruptured and enzymes deactivated by heating in a two tray cooker. The top tray was heated to 65–75° C. and the bottom tray to 91–95° C. using dry heat. A sweeping arm was used to agitate the material.

The oil was pressed from the flaked seed using a Simon-Rosedowns 9.5 cm diameter by 94 cm long screw press operating at a screw speed of 17 rpm. The crude oil was kept under nitrogen until further processing. Hexane extraction was used to remove the oil from the press cake. The press cake was extracted using a total residence time of 90 min. and a solvent to solids ration of 2.4:1. The crude solvent extracted oil was collected and kept under nitrogen until further processing.

The crude press and solvent extracted oils were dried and filtered to remove solids prior to degumming. The oils were heated at 100° C. under a vacuum until foaming stopped. The oil was cooled to 65–75° C. and 0.8% of filter aid was added and filtered. The oil was water degummed to remove phosphatides from the oil. The blended press and solvent extracted oils were heated to 60–70° C. and 2.0% of 80–100° C. water was added and mixed for 15 min. The oil was then centrifuged for gum removal.

Alkali refining was used to remove the free fatty acids. Phosphoric acid (85%) was added to 0.25% of the water degummed oil held at 60–70° C. and mixed for 30 min. Sodium hydroxide was added to the acid treated oil to neutralize the free fatty acids. After a 15 min. retention time the oil was heated to 75–80° C. and centrifuged.

Water washing was done to further remove soaps. The refined oil was washed by adding 15% of 90–95° C. water to the oil and mixed for 15 min. The oil was maintained at 75–80° C. and centrifuged. The washed oil was heated to 60–65° C. and bleached using Englehard's 'Grade 160' bleaching clay. The oil was heated to 105–110° C. and held under a vacuum for 30 min. The oil was cooled to 60–65° C. and 20% of the clay weight was added as a filter aid.

The bleached oil was deodorized using a Johnson-Loft packed tower continuous deodorizer. The oil deodorization temperature was 265° C. and the feed rate was 200 kg/hr. The steam rate was 1% of the feed rate and the system pressure was 0.16–0.18 kPa. The oil was preheated to 68–72° C. prior to being fed into the deareation vessel. The oil was cooled to 41–42° C. prior to removal of the vacuum. The oil was stored under nitrogen at −20° C.

The IMC 130 oil was analyzed for fatty acid composition via gas chromatography along with commercially available canola oils. Table 3 provides data on the fatty acid profiles of IMC 130 oil compared to commercially available canola oils, IMC 129 (a high oleic acid oil), IMC 144 (a typical generic canola oil) and Brand A (a typical generic canola oil). The data demonstrates reduced levels of linoleic ($C_{18:2}$), α-linolenic ($C_{18:3}$), and total polyunsaturated fatty acids for IMC 130.

TABLE 3

Fatty Acid Composition of Refined, Bleached and Deodorized Oils
Fatty Acid Composition (%)

| Variety | $C_{16:0}$ | $C_{18:0}$ | $C_{18:1}$ | $C_{18:2}$ | $C_{18:3}$ | Total Polys* |
|---|---|---|---|---|---|---|
| IMC 130 | 3.6 | 2.9 | 76.2 | 10.3 | 3.4 | 13.7 |
| IMC 144 | 2.9 | 2.1 | 62.6 | 19.5 | 8.1 | 27.6 |
| IMC 129 | 3.9 | 2.0 | 78.8 | 7.7 | 3.9 | 11.6 |
| Brand A | 3.8 | 2.0 | 60.9 | 19.9 | 9.1 | 28.0 |

*Total polyunsaturated acids

Oils were evaluated for AOM hours under the methods outlined in the American Oil Chemists' Society (AOCS) Official Method Cd 12-57 for *Fat Stability:Active Oxygen Method* (re'vd. 1989). The degree of oxidative stability is rated as the number of hours to reach a peroxide value of 100. Each oil sample was prepared in duplicate.

The IMC 130 oil was found to have significantly higher AOM hours than other oils tested, IMC 144, IMC 01, and IMC 129 after similar pilot plant processing. The IMC 144, IMC 01, and IMC 129 oils are currently commercially available from InterMountain Canola, Cinnaminson, N.J. (Table 4). IMC 129 (a high oleic variety) and IMC 01 (a low α-linolenic variety) were the parent lines crossed to generate IMC 130. IMC 144 is a typical generic canola oil. IMC 130 oil has a minimum of 37 AOM hours which is significantly greater than commercial-type, generic canola at 22 AOM hours. Typically, pilot plant processing of oils tends to reduce AOM hours as the process is much harsher on the oil than commercial processing. The greater oxidative stability of IMC 130 can be attributed to a lower polyunsaturated fatty acid content than the IMC 144 oil or typical generic canola oil (Table 3). The greater oxidative stability over the high oleic IMC 129 oil, which is similar in fatty acid composition to IMC 130 oil, indicates that oxidative stability is not solely related to fatty acid content.

TABLE 4

AOM Hours of Pilot Plant Processed Canola Oils

| Process Method | IMC 144 (Generic) | IMC 01 (Low ALA)* | IMC 129 (High Oleic) | IMC 130 (Example 1) |
|---|---|---|---|---|
| Pilot Plant | 15–22 | 20–22 | 16 | 37–40 |

*ALA = α-linolenic acid

Example 2

The oil of Example 1 and IMC 144, a generic canola oil, were subjected to further testing to determine frying stability as measured by oxidative degradation during frying.

1900 g of each test oil was placed in a clean six quart capacity 110 volt, commercial fryer (Tefal Super Cool Safety Fryers Model 3617). Oil temperature was maintained at 190° C. for eight hours each day. Temperature was controlled to ±5° C. of the target temperature using a Cole-Palmer temperature controller.

Commercially available frozen french fries (100 g) were fried for four min, three times per eight hour day in each test oil. 50 mL of oil were removed each day for chemical analysis to determine the amount of oxidative degradation. Fresh oil was added to the fryer each day to replace the amount removed for samples or lost through absorption on fries and retention on process equipment.

The oxidative parameters of the oils after frying were measured using procedures established by the AOCS (Official Methods and Recommended Practices of the American Oil Chemists' Society, Fourth Edition (1989) Ed., D. Firestone, Published by the American Oil Chemists' Society, Champaign, Ill.). These oxidative parameters are indicators of fry stability.

The oil was analyzed after frying for Total Polar Material (%TPM), Free Fatty Acids (%FFA), Color Development and Para-Anisidine Value (P-AV). The resulting data at 0, 32, and 64 hours of frying is reported in Table 5. The IMC 130 values reported in Table 5 are significantly lower than the IMC 144 values with a 95% degree of confidence. This demonstrates the improved fry stability of IMC 130 oil over commercial IMC 144 canola oil.

The percent of total polar material was determined using the AOCS Official Method Cd 20-91. The total polar materials are a measure of the total amount of secondary by-products generated from the triacylglycerols as a consequence of oxidations and hydrolysis. Reduced accumulation of total polar material by an oil indicates improved oxidative stability. IMC 130 was significantly reduced in total polar material after 32 and 64 hours of frying in comparison to commercial canola oil.

The percent of free fatty acids were determined using AOCS Official Method Ca 5a0-40. Free fatty acids generated in the oil during frying is a measure of oxidation and hydrolysis of the triacylglycerols. Reduced free fatty acids during frying of an oil indicates improved oxidative stability. In comparison to commercial canola oil, IMC 130 oil was significantly reduced in free fatty acids after 32 and 64 hours of frying.

Color development was measured using the AOCS Official Method Cc 13b-45 using a Lovibond Tintometer and is reported as red color. Red color development in the oil during frying is an indication of triacylglycerol oxidation. Oils with reduced red color development will have improved oxidative stability. IMC 130 oil had significantly less red color development than the commercial oil after 32 and 64 hours of frying.

The para-anisidine value was measured using the AOCS Official Method Cd 18-90. Aldehydes are generated during frying from the oxidation of the triacylglycerol are measured by the p-anisidine value. The p-anisidine value is 100 times the optical density measured at 350 nm in a 1 cm cell of a solution containing 1.00 g of the oil in 100 mL of a mixture of solvent and reagent according to the method referenced, and is in absorbance/g. Reduced development of aldehydes during frying is an indicator of improved oxidative stability of the oil. IMC 130 had significantly less aldehyde content after 32 and 64 hours of frying than the IMC 144 canola oil, a typical commercial generic canola oil.

TABLE 3

Effects of Frying on Oxidative Parameters

| Oxidation Parameter | IMC 130 at 0 Hrs. | IMC 144 at 0 Hrs. | IMC 130 at 32 Hrs. | IMC 144 at 32 Hrs. | IMC 130 at 64 Hrs. | IMC 144 at 64 Hrs. |
|---|---|---|---|---|---|---|
| % TPM[a] | 5.3 | 5.8 | 12.0 | 18.2 | 22.6 | 27.2 |
| % FFA[b] | 0.01 | 0.01 | 0.29 | 0.46 | 0.74 | 0.96 |
| Lovibond Color[c] | 0.3 | 0.5 | 2.7 | 4.3 | 6.7 | 12.5 |
| P-AV[d] | 0.27 | 1.65 | 112 | 164 | 125 | 145 |

[a] Total polar material, %
[b] Free fatty acids, %
[c] Lovibond color, red
[d] para-anisidine value, absorbance/g Example 3

The oil of Example 5 plus the following oils were subjected to further testing.

IMC 129—high oleic canola oil Quality analysis of each oil is found in Table 6.

TABLE 6

Oil Analysis

| | IMC 130 | IMC 129 |
|---|---|---|
| Red Color | 0.8 | 0.3 |
| Yellow Color | 6 | 2 |
| para-anisidine value[3] | 2.58 | 0.66 |
| Peroxide Value[1] | 0.3 | 0.3 |
| Totox Value[2] | 3.18 | 1.24 |
| % Polars | 0.69 | .64 |
| % Polymers | 0.013 | 0.010 |
| % Free Fatty Acids | 0.022 | 0.014 |
| % C16:0 | 3.5 | 3.6 |
| % C18:0 | 2.3 | 2.0 |
| % C18:1 | 73.4 | 75.7 |
| % C18:2 | 11.1 | 9.5 |
| % C18:3 | 5.7 | 6.2 |

[1] Peroxide Value, meq/Kg
[2] Totox Value = para-anisidine value + 2 (peroxide value)
[3] para-anisidine value, absorbance per gram Oxidative stability of the oil in Example 5 was demonstrated by measuring the increase in Peroxide Value and in para-Anisidine Value generated under accelerated aging conditions using a modified Schaal oven test. The test oil (200 g) was placed in an 500 ml uncovered amber glass bottle with a 4.3 cm opening, and placed in a 60° C. convection oven. One bottle was prepared for each evaluation. Results are found in Table 7 and Table 8.

The peroxide value was measured using the AOCS Official Method Cd 8b-90. Hydroperoxides generated from oxidation of the triacylglycerols were measured by the peroxide value. The peroxide value was expressed in terms of milliequivalents of peroxide per 1000 grams of sample (meq/Kg). Reduced development of hydroperoxides during storage was an indicator of improved oxidative stability.

The para-anisidine value was measured using the AOCS Official Method Cd 18-90. Aldehydes generated from the oxidation of the triacylglycerol was measured by the p-anisidine value. The p-anisidine value was 100 times the optical density measured at 350 nm in a 1 cm cell of a solution containing 1.00 g of the oil in 100 ml of a mixture of solvent and reagent according to the method referenced, and is absorbance/g. Reduced development of aldehydes during storage was an indicator of improved oxidative stability of the oil.

TABLE 7

Accelerated Aging - Oxidative Stability
Increase in Peroxide Value, Milliequivalents per kg

| Days in oven: | IMC 130 | IMC 129 |
|---|---|---|
| 3 | 0.9 | 0.7 |
| 6 | 2.1 | 2.3 |
| 9 | 12.6 | 14.9 |
| 12 | 16.1 | 22.1 |
| 15 | 24.5 | 29.7 |

TABLE 8

Accelerated Aging - Oxidative Stability
Increase in para-Anisidine Value, Absorbance per g

| Days in oven: | IMC 130 | IMC 129 |
|---|---|---|
| 6 | 0.1 | 0.2 |
| 9 | 2.0 | 3.1 |
| 12 | 4.8 | 6.9 |
| 15 | 6.9 | 10.2 |

Example 4

The oil of Example 5 plus the following oils were tested for oxidative stability.

Brand T—commercially available high oleic sunflower oil
Brand A—commercially available generic canola oil
Quality analysis of each oil is found in Table 9.

Oxidative stability of the oils described in Table 9 were determined under accelerated aging conditions using a modified Schaal oven test which accelerates oxidation. Oxidative stability was demonstrated by the increase in peroxide value over the test period. Schaal oven tests show that each day of accelerated oxidation at 60° C. is equivalent to a month of oxidation under ambient storage conditions. Using this correlation three days of accelerated aging is equivalent to three months of ambient storage. The test oil (200 g) was placed in a 500 ml uncovered amber glass bottle with a 4.3 cm opening, and placed in a 60° C. convection oven. One bottle was prepared for each evaluation. The test was carried out to six days to simulate actual product shelf-life of six months. Results are found in Table 10.

The peroxide value was measured using the AOCS Official Method Cd 8b-90. Hydroperoxides generated from oxidation of the triacylglycerols were measured by the peroxide value. The peroxide value was expressed in terms of milliequivalents of peroxide per 1000 grams of sample (meq/Kg). Reduced development of hydroperoxides during storage is an indicator of improved oxidative stability. IMC 130 had significantly less peroxide development after three days and six days in the Schaal oven test than Brand T, a high oleic sunflower oil with lower polyunsaturates ($C_{18:2}$+ $C_{18:3}$), and Brand A, a typical commercial generic canola oil.

TABLE 9

Quality Analysis of Test Oils

| | IMC 130 | Brand T | Brand A |
|---|---|---|---|
| Red Color | 0.8 | 0.8 | 0.7 |
| Yellow Color | 6 | 6 | 5 |
| para-anisidine value[3] | 2.58 | 4.21 | 2.32 |
| Peroxide Value[1] | 0.3 | 0.6 | 0.7 |
| Totox Value[2] | 3.18 | 5.41 | 3.72 |
| % Polars | 0.69 | 0.90 | 0.36 |
| % Polymers | 0.013 | 0.004 | 0.01 |
| % Free Fatty Acids | 0.022 | 0.016 | 0.013 |
| % C16:0 | 3.5 | 3.3 | 4.0 |
| % C18:0 | 2.3 | 4.2 | 2.0 |
| % C18:1 | 73.4 | 81.7 | 62.5 |
| % C18:2 | 11.1 | 8.8 | 18.3 |
| % C18:3 | 5.7 | 0.3 | 7.7 |

[1]peroxide Value, meq/Kg
[2]Totox Value = para-anisidine value + 2 (peroxide value)
[3]para-anisidine value, absorbance/g

TABLE 10

Accelerated Aging - Oxidative Stability
Increase in Peroxide Value, Meq/Kg

| Days in Oven: | IMC 130 | Brand A | Brand T |
|---|---|---|---|
| 3 | 0.8 | 6.2 | 3.2 |
| 6 | 1.8 | 14.4 | 7.0 |

Example 5

IMC 130 canola seed was produced during the 1993 growing season of the Northwestern U.S. The resulting IMC 130 canola seed was cleaned through commercial seed cleaning equipment to remove foreign matter consisting of weed seeds, canola plant material, immature canola seed and other non canola matter.

The cleaned IMC 130 canola seed was crushed and the resulting oil was processed at SVO Specialty Products, Inc., One Mile East, Culbertson, Mont. Approximately 361 tons of IMC 130 canola seed was crushed under the processing conditions outlined below.

Whole canola seed was passed through a double roll Bauermeister flaking rolls with smooth surface rolls available from Bauermeister Inc., Memphis, Tenn. 38118. The roll gap was adjusted so as to produce a canola flake 0.25 to 0.30 mm thickness. Flaked canola seed was conveyed to a five tray, 8 foot diameter stacked cooker, manufactured by Crown Iron Works, Minneapolis, Minn. 55440. The flaked seed moisture was adjusted in the stacked cooker to 5.5–6.0%. Indirect heat from the steam heated cooker trays was used to progressively increase the seed flake temperature to 80–90° C., with a retention time of approximately 20–30 minutes. A mechanical sweep arm in the stacked cooker was used to ensure uniform heating of the seed flakes. Heat was applied to the flakes to deactivate enzymes, facilitate further cell rupturing, coalesce the oil droplets and agglomerate protein particles in order to ease the extraction process.

Heated canola flakes were conveyed to a screw press from Anderson International Corp., Cleveland, Ohio 44105 equipped with a suitable screw worm assembly to reduce press out approximately 70% of the oil from the IMC 130 canola flakes. The resulting press cake contained 15.0–19.0% residual oil.

Crude oil produced from the pressing operation was passed through a settling tank with a slotted wire drainage top to remove the solids expressed out with the oil in the screw pressing operation. The clarified oil was passed through a plate and frame filter to remove the remaining fine solid canola particles. The filtered oil was combined with the oil recovered from the extraction process before oil refining.

Canola press cake produced from the screw pressing operation was transferred to a FOMM basket extractor available from French Oil Mill and Machinery Co., Piqua, Ohio 45356, where the oil remaining in the cake was extracted with commercial n-Hexane at 55° C. Multiple counter current hexane washes were used to substantially remove the remaining oil in the press cake, resulting in a press cake which contained 1.2–2.3%, by weight, residual oil in the extracted cake. The oil and hexane mixture (miscella) from the extraction process was passed through a two stage rising film tube type distillation column to distill the hexane from the oil. Final hexane removal from the oil was achieved by passing the oil through a stripper column containing disk and doughnut internals under 23–26 in. Hg vacuum and at 107–115° C. A small amount of stripping steam was used to facilitate the hexane removal. The canola oil recovered from the extraction process was combined with the filtered oil from the screw pressing operation, resulting in blended crude oil, and was transferred to oil processing.

In the oil processing the crude oil was heated to 66° C. in a batch refining tank to which 0.15% food grade phosphoric acid, as 85% phosphoric acid, was added. The acid serves to convert the non hydratable phosphatides to a hydratable form, and the chelate minor metals that are present in the crude oil. The phosphatides and the metal salts are removed from the oil along with the soapstock. After mixing for 60 minutes at 66° C., the oil acid mixture was treated with sufficient sodium hydroxide solution (12° Be) to neutralize the free fatty acids and the phosphoric acid in the acid oil mixture. This mixture was heated to 71° C. and mixed for 35 minutes. The agitation was stopped and the neutralized free fatty acids, phosphatides, etc. (soapstock) were allowed to settle into the cone bottom of the refining tank for 6 hours. After the settling period, the soapstock was drained off from the neutralized oil.

A water wash was done to reduce the soap content of the oil by heating the oil to 82° C. and by adding 12% hot water. Agitation of the mixture continued for 10 minutes. The mixture was allowed to settle out for 4 hours at which time the water was drained off the bottom of the refining vessel.

The water washed oil was heated to 104–110° C. in a vacuum bleacher vessel maintained at 24–26 in. Hg vacuum. A slurry of the IMC 130 canola oil and Clarion 470 bleaching clay available from American Colloid Company, Refining Chemicals Division, Arlington Heights, Ill. 60004, was added to the oil in the vacuum bleacher. This mixture was agitated for 20 minutes before filtering to remove the bleaching clay. The clay slurry addition was adjusted to provide a Lovibond color AOCS Official Method Cc 136-4 of less than 1.0 red units when the oil was heated to 288° C. under atmospheric pressure. Nitrogen was injected into the filtered bleached oil and maintained under a nitrogen blanket until the oil was deodorized.

Refined and bleached IMC 130 canola oil was deodorized in a semi-continuous Votator deodorizer tower at a rate of approximately 7,000 pounds per hour. The deodorization temperature was maintained at 265–268° C. with a system pressure of 0.3–0.5 mm Hg absolute pressure. Approximately 1–1.5% sparge steam was used to strip off the free fatty acids, color bodies, and odor components. Retention time in the deodorizer was 50–70 minutes. The deodorized oil was cooled to 45–50° C. and nitrogen was injected prior to removal of the vacuum. The deodorized oil was stored under a nitrogen blanket.

The resulting IMC 130 deodorized oil was analyzed for fatty acid composition via gas chromatography. The percent fatty acids were $C_{16:0}$ of 3.6%, $C_{18:0}$ of 2.2%, $C_{18:1}$ of 74.3%, $C_{18:2}$ of 11.9%, $C_{18:3}$ of 4.8% and total polyunsaturated of 16.7%. These data can be compared to the values for IMC 144, IMC 129 and Brand A as shown in Table 3. The data demonstrate that IMC 130 maintains reduced levels of linolenic acid ($C_{18:2}$), α-linolenic ($C_{18:3}$), and total polyunsaturated fatty acids when compared to typical generic canola oils IMC 144 and Brand A.

Table 11 provides data on the AOM hours of the IMC 130 oil processed as described above (the commercial process in 1993), compared to commercially available canola oils, IMC 129 (a high oleic acid oil), IMC 144 (a typical generic canola oil) and IMC 01 (a low α-linolenic oil). The IMC 130 oil was evaluated for AOM hours under the methods outlined in the American Oil Chemists' (AOCS) Official Method Cd 12-57 for Fat Stability: Active Oxygen Method (re'vd 1989). The degree of oxidative stability is rated as the number of hours to reach a peroxide value of 100. The higher AOM hours of IMC 130 reflects its greater oil stability. Each oil sample was prepared in duplicate.

TABLE 11

AOM Hours of Commercially Processed Canola Oils

| Process Method | IMC 144 (Generic) | IMC 01 (Low ALA)* | IMC 129 (High Oleic) | IMC 130 (Example 5) |
|---|---|---|---|---|
| Commercial | 15–18 | 30 | 30 | 37.5 |

*ALA = α-linolenic acid

Example 6

Another doubled haploid line was identified in the $DH_2$ generation of the IMC129×IMCO1 cross of Example 1 and termed A13.30137. The line was self-pollinated and selected as described in Example 1 for five generations. A13.30137 was tested for fatty acid stability and yield potential in research plots and strip trials in Idaho, Montana, and Washington. It appeared homogeneous and morphological variation was not observed during the production of foundation seed.

A13.30137 matured about two days earlier than IMC130 and was about 10 cm shorter than IMC130. The fatty acid composition of A13.30137 seeds was determined over 6 generations as described in Example 1 and is shown in Table 12. The yield performance of A12.30137 in research plots and strip trials is shown in Table 13 for the $DH_5$ generation and in Table 14 for the $DH_7$ generation.

TABLE 12

Fatty Acid Composition of A13.30137 from $DH_2$ to $DH_7$ Generation

| Generation | Fatty Acid Composition | | | | | |
|---|---|---|---|---|---|---|
| | $C_{16:0}$ | $C_{18:0}$ | $C_{18:1}$ | $C_{18:2}$ | $C_{18:3}$ | $C_{22:1}$ |
| DH2 | 3.8 | 2.1 | 76.2 | 11.5 | 3.2 | 0.00 |
| DH3 | 3.4 | 1.9 | 76.8 | 10.7 | 3.7 | 0.00 |
| DH4 | 3.2 | 1.8 | 77.1 | 9.8 | 3.5 | 0.00 |
| DH5* | 3.5 | 2.2 | 75.0 | 10.1 | 5.3 | 0.00 |

TABLE 12-continued

Fatty Acid Composition of A13.30137 from $DH_2$ to $DH_7$ Generation

| Generation | Fatty Acid Composition | | | | | |
|---|---|---|---|---|---|---|
| | $C_{16:0}$ | $C_{18:0}$ | $C_{18:1}$ | $C_{18:2}$ | $C_{18:3}$ | $C_{22:1}$ |
| DH6* | 3.5 | 1.7 | 75.3 | 10.2 | 4.9 | 0.00 |
| DH7 | 3.6 | 2.4 | 76.7 | 10.2 | 3.8 | 0.00 |

*Lower temperatures during growing season.

TABLE 13

Yield Performance of A13.30137 $DH_5$ Generation

| Line Name | Yield (lb/acre) | % of Westar |
|---|---|---|
| Hyola 401 | 2,171 | 118 |
| A13.30137 | 1,879 | 102 |
| 1MC129 | 1,865 | 102 |
| Westar | 1,835 | 100 |
| Legend | 1,764 | 96 |
| IMC130 | 1,573 | 86 |
| Global | 1,526 | 83 |

TABLE 14

Yield Performance of A13.30137 DH7 Generation

| Line Name | Yield (lb/acre) | % of Checks* |
|---|---|---|
| Cyclone | 1,960 | 131 |
| Hyola 401 | 1,876 | 126 |
| A13.30137 | 1,871 | 122 |
| Delta | 1,859 | 121 |
| Legend | 1,804 | 118 |
| 1MC129 | 1,783 | 110 |
| IMC130 | 1,625 | 96 |
| Excel | 1,578 | 93 |

*Average combined performance of Delta, Cyclone, Excel and Legend = 100.

What is claimed is:

1. A non-hydrogenated canola oil having an oleic acid content of about 74% to about 80% and a Totox value of greater than 3.0.

2. The oil of claim 1, wherein said oil has an oxidative stability of about 35 to about 40 AOM hours in the absence of added antioxidants.

3. The oil of claim 1, wherein said oil has a linoleic acid content of about 5% to about 12%.

4. The oil of claim 1, wherein said canola oil has an α-linolenic acid content of about 2% to about 5%.

5. A non-hydrogenated canola oil, said oil having an oleic acid content of about 74% to about 80% and a peroxide value that increases by a maximum of about 24.5 Meq/kg after accelerated aging for 15 days.

6. The oil of claim 5, wherein said oil has an oxidative stability of about 35 to about 40 AOM hours in the absence of added antioxidants.

7. The oil of claim 5, wherein said oil has a linoleic acid content of about 5% to about 12%.

8. The oil of claim 5, wherein said canola oil has an α-linolenic acid content of about 2% to about 5%.

* * * * *